US008323697B2

(12) United States Patent
Rosenfeldt et al.

(10) Patent No.: US 8,323,697 B2
(45) Date of Patent: Dec. 4, 2012

(54) PLANT PROTECTION GRANULATES TO BE APPLIED TO LEAF SURFACE

(75) Inventors: Frank Rosenfeldt, Langenfeld (DE); Guillaume Huchet, Lawrence, KS (US); Claudia Letmathe, Bergisch Gladbach (DE); Axel Eble, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 280 days.

(21) Appl. No.: 12/515,486

(22) PCT Filed: Nov. 14, 2007

(86) PCT No.: PCT/EP2007/009825
§ 371 (c)(1),
(2), (4) Date: Jun. 23, 2009

(87) PCT Pub. No.: WO2008/061655
PCT Pub. Date: May 29, 2008

(65) Prior Publication Data
US 2009/0274767 A1 Nov. 5, 2009

(30) Foreign Application Priority Data
Nov. 24, 2006 (DE) .......................... 10 2006 055 477

(51) Int. Cl.
*A61K 9/14* (2006.01)
(52) U.S. Cl. ....................................................... 424/489
(58) Field of Classification Search .................. None
See application file for complete search history.

(56) References Cited

U.S. PATENT DOCUMENTS 3,843,783 A 10/1974 Burlow

FOREIGN PATENT DOCUMENTS

| CA | 1040451 | * | 10/1978 |
|---|---|---|---|
| DE | 3739088 | | 6/1989 |
| EP | 0361163 | | 4/1990 |
| EP | 0404727 | | 12/1990 |
| EP | 0408501 | | 1/1991 |
| EP | 1379137 | | 1/2004 |
| GB | 1566854 | | 5/1980 |
| JP | 62120301 | * | 6/1987 |
| JP | 01157903 | | 6/1989 |
| JP | 07247202 | * | 9/1995 |
| JP | 09194302 | * | 7/1997 |
| WO | 8504074 | | 9/1985 |
| WO | 8900601 | | 1/1989 |
| WO | 8904842 | | 6/1989 |
| WO | WO-9215285 | * | 9/1992 |
| WO | 9301713 | | 2/1993 |
| WO | 9319023 | | 9/1993 |
| WO | 0202742 | | 1/2002 |
| WO | 2007081695 | | 7/2007 |

OTHER PUBLICATIONS

International Search Report Relating to PCT/EP2007/009825 dated Feb. 19, 2009.

* cited by examiner

*Primary Examiner* — Alton Pryor
(74) *Attorney, Agent, or Firm* — Baker Donelson Bearman, Caldwell & Berkowitz, PC

(57) ABSTRACT

The present invention relates to granules for application to the leaf surface, and to a process for their preparation. The invention furthermore relates to the use of these granules for foliar penetration or the formulation of baits.

19 Claims, No Drawings

PLANT PROTECTION GRANULATES TO BE APPLIED TO LEAF SURFACE

CROSS REFERENCE TO RELATED APPLICATIONS

This application is a §371 National Stage Application of PCT/EP2007/009825 Nov. 14, 2007 which claims priority to German Application 10 2006 055 477.9 filed Nov. 24, 2006.

BACKGROUND OF THE INVENTION

1. Field of the Invention

The present invention relates to granules for application to the leaf surface, and to a process for their preparation. The invention furthermore relates to the use of these granules for foliar penetration or the formulation of baits.

2. Description of Related Art

Plant protection products are usually applied as spray mixtures, which means that the formulation of the active substance is sprayed onto the leaf surfaces of plants in the form of a liquid system or a spray. However, the handling of spray mixtures is complicated, requires specialist equipment and is not user-friendly. What is more, the result of spray drift is that not only the area to be treated is sprayed, but droplets of the plant protection formulations also arrive in an uncontrolled manner in adjacent areas. To avoid these spray drifts, and to make the handling and the use of crop protection products safer, simpler and more user-friendly, the plant protection products should therefore preferably be applied in the form of granules in order to simultaneously improve the public acceptance of the use of plant protection products.

Agrochemical granules furthermore have the advantage that they are readily discernible after application of the granules so that one can see whether a field has been treated or not. Moreover, the use of granules comprising agrochemical active substances is simpler than the use of corresponding aqueous or emulsion-containing solutions.

The disadvantage to date of the use of granules comprising agrochemical active substances is that a multiplicity of agrochemical active substances only have a biological effect when they are applied directly to the leaf surface and taken up by the plant via foliar penetration. The granules known to date are unsatisfactory in this respect since the granules known to date do not adhere to the leaf surfaces upon application.

SUMMARY OF THE INVENTION

Accordingly, the object of the present invention was to provide plant protection products in the form of granules which can be applied directly to the leaf surface of plants, where they adhere by preference and where they release the active substance to the plant by preference.

This object is achieved by granules which contain at least one agrochemical active substance and hydrolysed starch.

The starch used in the granules according to the invention is preferably obtained from comminuted cereals (for example wheat, barley, maize, rye). Here, the starch mainly forms the matrix in the granules for the at least one agrochemical active substance to be used, and prevents the separation of active substance mixtures in their components.

DETAILED DESCRIPTION OF A PREFERRED EMBODIMENT

In a first embodiment of the present invention, the granules are designed such that they have, in terms of mass, a structure which is characterized by the particle sizes $x_{10}$ and $x_{90}$, where $x_{10}$ is generally greater than or equal to 100 μm, preferably greater than or equal to 200 μm, especially preferably greater than or equal to 300 μm, in particular greater than or equal to 350 μm, more preferably greater than or equal to 400 μm. The parameter $x_{10}$ which is shown for the granules according to the invention indicates the parameter which is not reached by no more than 10% by weight of the particles. Maintaining this order of magnitude is preferred for the granules according to the invention since the granules will, in such a case, be essentially free from dust and separation phenomena and therefore easier to handle.

In a further embodiment of the present invention, the structure of the granules has, in terms of mass, an $x_{90}$ size of generally less than 5 mm, preferably less than or equal to 2 mm, especially preferably less than or equal to 1.75 mm, in particular less than or equal to 1.2 mm, where the $x_{90}$ indicates the parameter which is exceeded by no more than 10% of the mass of the granule particles.

The granule density of the granules according to the invention is generally less than 1.5 kg/dm$^3$, preferably less than 1.4 kg/dm$^3$, especially preferably less than 1.3 kg/dm$^3$, in particular less than 1.0 kg/dm$^3$.

In principle, the agrochemical active substance used in the granules according to the invention is not subject to any restriction, and, within the scope of the present invention, it is possible to use all known agrochemical active substances in the granules. Examples are:

Fungicides:

Nucleic acid synthesis inhibitors:

benalaxyl, benalaxyl-M, bupirimat, chiralaxyl, clozylacon, dimethirimol, ethirimol, furalaxyl, hymexazol, mefenoxam, metalaxyl, metalaxyl-M, ofurace, oxadixyl, oxolinic acid.

Mitosis and cell division inhibitors benomyl, carbendazim, diethofencarb, ethaboxam, fuberidazole, pencycuron, thiabendazole, thiophanate-methyl, zoxamid Respiratory chain complex I inhibitors diflumetorim Respiratory chain complex II cnhibitors boscalid, carboxin, fenfuram, flutolanil, furametpyr, furmecyclox, mepronil, oxycarboxin, penthiopyrad, thifluzamid Respiratory chain complex III inhibitors azoxystrobin, cyazofamid, dimoxystrobin, enestrobin, famoxadon, fenamidon, fluoxastrobin, kresoxim-methyl, metominostrobin, orysastrobin, pyraclostrobin, picoxystrobin, trifloxystrobin Decouplers dinocap, fluazinam ATP production inhibitors fentin acetate, fentin chloride, fentin hydroxide, silthiofam Amino acid and protein biosynthesis inhibitors andoprim, blasticidin-S, cyprodinil, kasugamycin, kasugamycin hydrochloride hydrate, mepanipyrim, pyrimethanil Signal transduction inhibitors fenpiclonil, fludioxonil, quinoxyfen Lipid and membrane synthesis inhibitors chlozolinate, iprodion, procymidon, vinclozolin ampropylfos, ampropylfos-potassium, edifenphos, etridiazol, iprobenfos (IBP), isoprothiolane, pyrazophos tolclofos-methyl, biphenyl iodocarb, propamocarb, propamocarb hydrochloride, propamocarb-fosetylate Ergosterol biosynthesis inhibitors
fenhexamid,
azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil-sulphate, imibenconazole, ipconazole, metconazole, myclobutanil, nuarimol, oxpoconazole, paclobutrazole, penconazole, pefurazoate prochloraz, propiconazole, prothioconazole, pyrifenox, simeconazole, tebuconazole, tetraconazole, triadimefon, triadimenol, triflumizol, triforine, triticonazole, uniconazole, voriconazole, viniconazole,
aldimorph, dodemorph, dodemorph-acetate, fenpropidin, fenpropimorph, spiroxamin, tridemorph,
naftifin, pyributicarb, terbinafin Cell wall synthesis inhibitors
benthiavalicarb, bialaphos, dimethomorph, flumorph, iprovalicarb, mandipropamid, polyoxins, polyoxorim, validamycin A Melanin biosynthesis inhibitors
capropamid, diclocymet, fenoxanil, phthalide, pyroquilon, tricyclazole Resistance induction
acibenzolar-S-methyl, probenazole, tiadinil Multi-site
captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadin, iminoctadin albesilat, iminoctadin triacetate, mancopper, mancozeb, maneb, metiram, metiram-zinc, propineb, sulphur and sulphur preparations comprising calcium polysulphide, thiram, tolylfluanid, zineb, ziram Other fungicides
amibromdol, benthiazole, bethoxazin, capsimycin, carvone, quinomethionate, chloropicrin, cufraneb, cyflufenamid, cymoxanil, dazomet, debacarb, diclomezine, dichlorophen, dicloran, difenzoquat, difenzoquat methylsulphate, diphenylamine, ferimzon, flumetover, flusulfamid, fluopicolid, fluoroimid, fosetyl-aluminium, fosetyl-calciurn, fosetyl-sodium, hexachlorobenzene, 8-hydroxyquinolin sulphate, irumamycin, methasulphocarb, metrafenon, methyl isothiocyanate, mildiomycin, natamycin, nickel dimethyldithiocarbamate, nitrothal-isopropyl, octhilinone, oxamocarb, oxyfenthiin, pentachlorophenol and its salts, 2-phenylphenol and its salts, piperalin, propanosin-sodium, proquinazid, pyribencarb, pyrrolonitrine, quintozene, tecloftalam, tecnazene, triazoxide, trichlamid, valiphenal, zarilamide,
2-(2-{[6-(3-chloro-2-methylphenoxy)-5-fluoropyrimidin-4-yl]oxy}phenyl)-2-(methoxyimino)-N-methylacetamide,
2-[[[[1-[3(1-fluoro-2-phenylethyl)oxy]phenyl]ethylidene]amino]oxy]methyl]alpha-(methoxyimino)-N-methyl-alpha-benzacetamide,
cis-1-(4-chlorophenyl)-2-(1H-1,2,4-triazol-1-yl)cycloheptanol,
1-[(4-methoxyphenoxy)methyl]-2,2-dimethylpropyl-1H-imidazole-1-carboxylic acid,
2,3,5,6-tetrachloro-4-(methylsulphonyl)pyridine,
2-butoxy-6-iodo-3-propylbenzopyranon-4-one,
2-chloro-N-(2,3-dihydro-1,1,3-trimethyl-1H-inden-4-yl)-3-pyridinecarboxamide,
3,4,5-trichloro-2,6-pyridinecarhonitrile,
3,4-dichloro-N-(2-cyanophenyl)isothiazole-5-carboxamide (isotianil)
3-[5-(4-chlorophenyl)-2,3-dimethylisoxazolidin-3-yl]pyridine,
5-chloro-6-(2,4,6-trifluorophenyl)-N-[(1R)-1,2,2-trimethylpropyl][1,2,4]triazolo[1,5-a]pyrimidin-7-amine,
5-chloro-7-(4-methylpiperidin-1-yl)-6-(2,4,6-trifluorophenyl)[1,2,4]triazolo[1,5-a]pyrimidine,
5-chloro-N-[(1R)-1,2-dimethylpropyl]-6-(2,4,6-trifluorophenyl)[1,2,4]triazolo[1,5-a]pyrimidin-7-amine,
methyl 2-[[[cyclopropyl[(4-methoxyphenyl)imino]methyl]thio]methyl]-alpha-(methoxymethylene)-benzacetate,
methyl 1-(2,3-dihydro-2,2-dimethyl-1H-inden-1-yl)-1H-imidazole-5-carboxylate,
N-(3',4'-dichloro-5-fluorobiphenyl-2-yl)-3-(difluoromethyl)-1-methyl-1H-pyrazole4-carboxamide,
N-(3-ethyl-3,5,5-trimethylcyclohexyl)-3-formylamino-2-hydroxybenzamide,
N-(4-chloro-2-nitrophenyl)-N-ethyl4-methylbenzenesulphonamide,
N-(4-chlorobenzyl)-3-[3-methoxy-4-(prop-2-yn-1-yloxy)phenyl]propanamide,
N-[(4-chlorophenyl)(cyano)methyl]-3-[3-methoxy-4-(prop-2-yn-1-yloxy)phenyl]propanamide,
N-(5-bromo-3-chloropyridin-2-yl)methyl-2,4-dichlornicotinamide,
N-[1-(5-bromo-3-chloropyridin-2-yl)ethyl]-2,4-dichloronicotinamide,
(2S)-N-[2-[4-[[3-(4-chlorophenyl)-2-propynyl]oxy]-3-methoxyphenyl]ethyl]-3-methyl-2-[(methylsulphonyl)amino]butanamide,
N-{(Z)-[(cyclopropylmethoxy)imino][6-(difluoromethoxy)-2,3-difluorophenyl]methyl}-2-benzacetamide,
N-{2-[1,1'-bi(cyclopropyl)-2-yl]phenyl}-3-(difluoromethyl)-1-methyl-1H-pyrazole-4-carboxamide,
N-{2-[3-chloro-5-(trifluoromethyl)pyridin-2-yl]ethyl}-2-(trifluoromethyl)benzamide,
N-ethyl-N-methyl-N'-{2-methyl-5-(trifluoromethyl)-4-[3-(trimethylsilyl)propoxy]phenyl}imido-formamide,
O-[1-[(4-methoxyphenoxy)methyl]-2,2-dimethylpropyl]-1H-imidazole-1-carbothioic acid,
2-amino-4-methyl-N-phenyl-5-thiazolecarboxamide,
2,4-dihydro-5-methoxy-2-methyl-4-[[[[1-[3-(trifluoromethyl)phenyl]ethylidene]amino]oxy]methyl]-phenyl]-3H-1,2,4-triazol-3-one (CAS No. 185336-79-2),
N-(6-methoxy-3-pyridinyl)cyclopropanecarboxamide.

Bactericides:
Bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
Acetylcholin esterase (AChE) inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metamsodium, methiocarb, methomyl, metolcarb, oxamyl, pirimicarb, promecarb, propoxur, thiodicarb, thiofanox, trimethacarb, XMC, xylylcarb, triazamate Organophosphates,
for example acephate, azamethiphos, azinphos (-methyl, -ethyl), bromophos-ethyl, bromofenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, suiprofos, tebupirimfos, temephos, terbufos, tetrachlorvinphos, thiometon, triazophos, triclorfon, vamidothion Sodium channel modulators/voltage-dependent sodium channel blockers
   pyrethroids,
   for example acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadetbrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralletbrin, tetramethrin (1R isomer), tralomethrin, transfluthrin, ZXI 8901, pyrethrins (pyrethrum)
   DDT
   Oxadiazines,
   for example indoxacarb
   semicarbazones,
   for example metaflumizon (BAS3201)
acetylcholine receptor agonists/antagonists
   chloronicotinyls,
   for example acetamiprid, clothianidin, dinotefuran, imidacloprid, nitenpyram, nithiazine, thiacloprid, thiamethoxam
   nicotins, bensultap, cartap
acetylcholine recptor modulators
   spinosyns,
   for example spinosad
GABA-controlled chloride channel antagonists
   organochlorines,
   for example camphecblor, chlordane, endosulfan, gamma-HCH, HCH, heptachlor, lindane, methoxychlor
   fiproles,
   for example acetoprole, ethiprole, fipronil, pyrafluprole, pyriprole, vaniliprole
   chloride channel activators
   mectins,
   for example abamectin, emamectin, emamectin-benzoate, ivermectin, lepimectin, milbemycin
   juvenile hormone mimetics,
   for example diofenolan, epofenonane, fenoxycarb, hydroprene, kinoprene, methoprene, pyriproxifen, triprene
   ecdysone agonists/disruptors
   diacylhydrazins,
   for example chromafenozide, halofenozide, methoxyfenozide, tebufenozide chitin biosynthesis inhibitors
   benzoyl ureas,
   for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron
   buprofezin
   cyrornazine
Oxidative phosphorylation inhibitors, ATP disruptors
   diafenthiuron
   organotin compounds,
   for example azocyclotin, cyhexatin, fenbutatin oxide
   uncouplers of oxidative phoshorylation by interrupting the H proton gradient
   pyrroles,
   for example chlorfenapyr
   dinitrophenols,
   for example binapacyrl, dinobuton, dinocap, DNOC, meptyldinocap
site-I electron transport inhibitors
   METIs,
   for example fenazaquin, fenpyroximate, pyrimidifen, pyridaben, tebufenpyrad, tolfenpyrad
   hydramethylnon
   dicofol
site-II electron transport inhibitors
   rotenone
site-III electron transport inhibitors
   acequinocyl, fluacrypyrim
microbial disruptors of the insect gut membrane
   *Bacillus thuringiensis* strains
lipid synthesis inhibitors
   tetronic acids,
   for example spirodiclofen, spiromesifen,
   tetramic acids,
   for example spirotetramate, cis-3-(2,5-dimethylphenyl)-4-hydroxy-8-methoxy-1-azaspiro[4.5]dec-3-en-2-one
   carboxamides,
   for example flonicamid
   octopaminergic agonists,
   for example amitraz
   inhibitors of magnesium-stimulated ATPase,
   propargite
   nereistoxin analogues,
   for example thiocyclam hydrogen oxalate, thiosultap-sodium
   ryanodin receptor agonists,
   benzoic acid dicarboxamides,
   for example flubendiamide
   anthranilamides,
   for example rynaxypyr (3-bromo-N-{4-chloro-2-methyl-6-[(methylamino)carbonyl]phenyl}-1-(3-chloropyridin-2-yl)-1H-pyrazole-5-carboxamide)
   biologicals, hormones or pheromones
   azadirachtin, *Bacillus* spec., *Beauveria* spec., codlemone, *Metarrhizium* spec., *Paecilomyces* spec., thuringiensin, *Verticillium* spec.
Active substances with unknown or unspecific mechanisms of action
   fumigants,
   for example aluminium phosphide, methyl bromide, sulphuryl fluoride
   antifeedants,
   for example cryolite, flonicamid, pymetrozine
   mite growth inhibitors,
   for example clofentezine, etoxazole, hexythiazox amidoflumet, benclothiaz, benzoximate, bifenazate, bromopropylate, buprofezin, chinomethionat, chlordimeform, chlorobenzilate, chloropicrin, clothiazoben, cyclopene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin.

Herbicides:

acetochlor; acifluorfen(-sodium); aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; aminopyralid, amitrole; AMS, i.e. ammonium sulphamate; anilofos; asulam; atrazine; azafenidin, azimsulphuron (DPX-A8947); aziprotryn; barbane; BAS 516 H, i.e. 5-fluoro-2-phenyl-4H-3,1-benzoxazin-4-one; beflubutamid, benazolin (-ethyl); benfluralin; benfuresate; bensulfuron (-methyl); bensulide; bentazone; benzobicyclon, benzofenap; benzofluor; benzoylprop (-ethyl); benzthiazuron; bialaphos; bifenox; bispyribac (-sodium), bromacil; bromobutide; bromofenoxim; bromoxynil; bromuron; buminafos; busoxinone; butachlor; butafenacil, butamifos; butenachlor; buthidazole; butralin; butroxydim, butylate; cafenstrole (CH-900); carbetamide; carfentrazone (-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon; chlorbromuron; chlorbufam; chlorfenac; chlorflurecol-methyl; chloridazon; chlorimuron(-ethyl); chlornitrofen; chiorotoluron; chloroxuron; chlorpropham; chlorsulfuron; chlorthal-dimethyl; chlorthiamid; chlortoluron, cinidon (-methyl and -ethyl), cinmethylin; cinosulfuron; clefoxydim, clethodim; clodinafop and its ester derivatives (for example clodinafop-propargyl); clomazone; clomeprop; cloproxydim; clopyralid; clopyrasulfuron (-methyl), cloransulam (-methyl), cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-D, 2,4-DB, dalapon; desmedipham; desmetryn; di-allate; dicamba; dichlobenil; dichlorprop; diclofop and its esters such as diclofop-methyl; diclosulam, diethatyl(-ethyl); difenoxuron; difenzoquat; diflufenican; diflufenzopyr, dimefuron; dimepiperate, dimethachlor; dimethametryn; dimethenamid (SAN-582H); dimethazone, dimexyflam, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HN-252); ethoxysulfuron, etobenzanid (HW 52); F5231, i.e. N-[2-chloro-4-fluoro-5-[4-(3-fluoropropyl)4,5-dihydro-5-oxo-1H-tetrazol-1-yl]phenyl]ethanesulphonamide; fenoprop; fenoxan, fenoxaprop and fenoxaprop-P and their esters, for example fenoxaprop-P-ethyl and fenoxaprop-ethyl; fenoxydim; fentrazamide, fenuron; flamprop (-methyl or -isopropyl or -isopropyl-L); flazasulfuron; floazulate, florasulam, fluazifop and fluazifop-P and their esters, for example fluazifop-butyl and fluazifop-P-butyl; flucarbazone (-sodium), fluchloralin; flumetsulam; flumeturon; flumiclorac (-pentyl), flumioxazin (S-482); flumipropyn; fluometuron, fluorochloridone, fluorodifen; fluoroglycofen (-ethyl); flupoxam (KNW-739); flupropacil (UBIC-4243); flupyrsulfuron (-methyl or -sodium), flurenol (-butyl), fluridone; flurochloridone; fluroxypyr (-meptyl); flurprimidol, flurtamone; fluthiacet (-methyl), fluthiamide, fomesafen; foramsulfuron, fosamine; furyloxyfen; glufosinate (-ammonium); glyphosate (-isopropylammonium); halosafen; halosulfuron (-methyl) and its esters (for example methyl ester, NC-319); haloxyfop and its esters; haloxyfop-P (=R-haloxyfop) and its esters; hexazinone; imazamethabenz(-methyl); imazapyr; imazaquin and salts such as the ammonium salt; imazamethapyr, imazamox, imazapic, imazethamethapyr; imazethapyr; imazosulfuron; indanofan, ioxynil; isocarbamid; isopropalin; isoproturon; isouron; isoxaben; isoxachlortole, isoxaflutole, isoxapyrifop; karbutilate; lactofen; lenacil; linuron; MCPA; MCPB; mecoprop; mefenacet; mefluidid; mesosulfuron, mesotrione, metamitron; metazachlor; methabenzthiazuron; metham; methazole; methoxyphenone; methyldymron; metabenzuron, methobenzuron; metobromuron; (alpha-)metolachlor; metosulam (XRD 511); metoxuron; metribuzin; metsulfuron-methyl; MH; molinate; monalide; monocarbamide dihydrogensulphate; monolinuron; monuron; MT 128, i.e. 6-chloro-N-(3-chloro-2-propenyl)-5-methyl-N-phenyl-3-pyridazinamine; MT 5950, i.e. N-[3-chloro4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron, oxaziclomefone, oxyfluorfen; paraquat; pebulate; pelargonic acid, pendimethatin; pentoxazone, perfluidone; phenisopham; phenmedipham; picloram; picolinafen, pinoxaden, piperophos; piributicarb; pirifenop-butyl; pretilachlor; primisulfuron (-methyl); procyazine; prodiamine; profluralin; proglinazine (-ethyl); prometone; prometryn; propachlor; propanil; propaquizafop and its esters; propazine; propham; propisochlor; propoxycarbazone (-sodium); propyzamide; prosulfalin; prosulfocarb; prosulfuron (CGA-152005); prynachlor; pyraflufen (-ethyl), pyrazolinate; pyrazone; pyrazosulfuron (-ethyl); pyrazoxyfen; pyribenzoxim, pyributicarb, pyridafol, pyridate; pyrimidobac (-methyl), pyrithiobac (-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; Ser. No. 106279, i.e. 2-[[7-[2-chloro-4-(trifluoromethyl)phenoxy]-2-naphthalenyl]oxy]propanoic acid and its methyl ester; sulcotrione, sulfentrazon (FMC-97285, F-6285); sulfazuron; sulfometuron (-methyl); sulfosate (ICI-A0224); sulfosulfuron, TCA; tebutam (GCP-5544); tebuthiuron; tepraloxydim, terbacil; terbucarb; terbuchlor; terbumeton; terbuthylazine; terbutryn; TFH 450, i.e. N,N-diethyl-3-[(2-ethyl-6-methylphenyl)sulphonyl]-1H-1,2,4-triazole-1-carboxamide; thenylchlor (NSK-850); thiafluamide, thiazafluron; thiazopyr (Mon-13200); thidiazimin (SN-24085); thifensulfuron (-methyl); thiobencarb; tiocarbazil; tralkoxydim, tri-allate; triasulfuron; triaziflam, triazofenamide; tribenuron (-methyl); triclopyr; tridiphane; trietazine; trifluralin; triflusulfuron and esters (for example methyl ester, DPX-66037); trimeturon; tritosulfuron, tsitodef; vemolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KHI-6127, KIH-485, KIH-2023 and SYN-523.

Here, the agrochemical active substances are given either by their common name in accordance with the International Organization for Standardization (ISO) or by their chemical name, if appropriate together with a customary code number.

In general, the concentration of the agrochemical active substance in the granules according to the invention is no less than 0.001% by weight, preferably no less than 0.005% by weight, especially preferably no less than 0.01% by weight, in particular no less than 0.05% by weight, based on the granules according to the invention. In a further embodiment, the maximum concentration of the agrochemical active substance in the granules according to the invention is, furthermore, generally no more than 10% by weight, preferably no more than 9% by weight, especially preferably no more than 8% by weight, in particular no more than 7% by weight, in each case based on the granules. The active substance concentration can be formed by one active substance or by a mixture of several active substances.

In principle, the granules according to the invention can take any shape, and is not limited in this respect. This means that not only irregular shapes, but also regular shapes, of the granules according to the invention are feasible. In this context, the granules may be present both as crushed granules and as cut granules. Regular shapes to be mentioned by way of example are the lenticular shape, a cylindrical shape, a spherical shape or a disc shape, by way of example.

Depending on the field of application of the granules according to the invention, the granules may comprise further additives. Examples of additives are adhesive additions, penetrants, fillers (extenders), lubricants, for example fats or oils, colorants, fragrances, release agents and preservatives.

In the event that adhesive additives are intended to be present in the granules according to the invention, the former are preferably selected from the group consisting of polyvinyl alcohols, polyvinyl acetates, carboxymethylcelluloses, natural and synthetic polymers in the form of powders, granules or latices, polyvinylpyrrolidone, vinylpyrrolidone/stryrene copolymers, vinylpyrrolidone/vinyl acetate copolymers, polyethylene glycol or inorganic adhesives. The adhesive additives are generally present in the mixture in concentrations of from 0 to 15% by weight, preferably from 0 to 10% by weight.

Penetrants which are suitable in accordance with the invention are defined by the fact that they promote the uptake of active substance from the dry or hydrated spray coating into the cuticle.

If penetrants are used in the granules according to the invention, the former may be selected for example among alkanol alkoxylates of the formula (I)

R—O-(-AO)$_m$—R'     (I)

in which

R represents straight-chain or branched alkyl having 4 to 20 carbon atoms,

R' represents H, methyl, ethyl, n-propyl, i-propyl, n-butyl, i-butyl, t-butyl, n-pentyl or n-hexyl, AO represents an ethylene oxide residue, a propylene oxide residue, a butylene oxide residue, or mixtures of ethylene oxide and propylene oxide residues, or mixtures of ethylene oxide and butylene oxide residues, and m represents numbers from 2 to 30.

The above formulae provide general definitions of the alkanol alkoxylates. These substances are mixtures of substances of the abovementioned type with different chain lengths. This is why averages, which may also deviate from integers, are calculated for the indices.

Preferably suitable are fatty alcohol ethoxylates of the general formula (I-1)

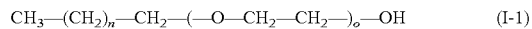

$CH_3$—$(CH_2)_n$—$CH_2$—(—O—$CH_2$—$CH_2$—)$_o$—OH     (I-1)

in which n represents average values of between 8.0 and 13.0, preferably 9.0 and 12.0, especially preferably 10.5, and o represents average values of between 6.0 and 17.0, preferably 7.0 and 9.0, especially preferably 8.4.

Suitable penetrants are described for example in EP 1 379 137 A, whose disclosure in this respect is incorporated into the present invention by reference.

Suitable penetrants are furthermore customary surface-active substances which are employed in formulations of agrochemical active substances. Examples which may be mentioned are ethoxylated nonylphenols, tributylphenol polyglycol ether, reaction products of alkyl phenols and ethylene oxide and/or propylene oxide, alkoxylated alkylamines, alkoxylated mono-, di- or triglycerides, polyethylene oxide sorbitan fatty acid esters, furthermore fatty acid polyglycol ether esters, diesters and diethers of polyalkylene oxides, fatty acid ester ethoxylates and alkyl ethoxylates and alkylaryl ethoxylates which may be phosphated and optionally neutralized with bases. Suitable anionic surfactants are furthermore all substances of this type which can conventionally be employed in agrochemical compositions. Preferred are alkali metal salts, ammonium salts and alkaline earth metal salts of alkylsulphonic acids or alkylarylsulphonic acids, and of alkyl (poly)ethylene glycol ether sulphates or alkyl (poly)ethylene glycol ether sulphonates. Non-surface-active penetrants which may be mentioned are fatty acid esters, mono- and diesters of dicarboxylic acids, and phosphate esters.

Fragrances which may be employed may be natural and synthetic fragrances. Natural fragrances, for example, may be selected from the group consisting of musk, civet, ambergris, castoreum and similar fragrances; ajowa oil, almond oil, absolute of ambrette seed, angelica root oil, aniseed oil, basil oil, bay oil, benzoin resinoid, essence of bergamot, birch oil, rosewood oil, absolute of common broom, cajeput oil, cananga oil, capsicum oil, caraway oil, cardamom oil, carrot seed oil, cassia oil, cedarwood oil, celery seed oil, cinnamon bark oil, citronella oil, clarisage oil, clove oil, cognac oil, coriander oil, cubeb oil, camphor oil, dill oil, tarragon oil, eucalyptus oil, sweet fennel oil, galbanum resinoid, garlic oil, geranium oil, ginger oil, grapefruit oil, hop oil, absolute of hyacinth, absolute of jasmine, juniper berry oil, labdanum resinoid, lavender oil, bayleaf oil, lemon oil, lemongrass oil, lovage oil, mace oil, mandarin oil, absolute of mimosa, absolute of myrrh, mustard oil, absolute of narcissus, neroli oil, nutmeg oil, absolute of oak moss, olibanum resinoid, onion oil, opoponax resinoid, orange oil, orange flower oil, concrete of iris, pepper oil, peppermint oil, Peru balsam, petite grain oil, pine needle oil, absolute of rose, rose oil, rosemary oil, sandlewood oil, sage oil, spearmint oil, styrax oil, thyme oil, balsam of tolu, absolute of tonka bean, absolute of tuberose, turpentine oil, absolute of vanilla pod, vetiver oil, absolute of violet leaves, ylang-ylang oil, and similar vegetable oils and the like.

Synthetic fragrances which may be added are:

pinene, limonene and similar hydrocarbons; 3,3,5-trimethylcyclohexanol, linalool, geraniol, nerol, citronellol, menthol, borneol, borneylmethoxycyclohexanol, benzyl alcohol, anisyl alcohol, cinnamyl alcohol, β-phenylethyl alcohol, cis-3-hexanol, turpineol and similar alcohols; anetholes, musk xylene, isoeugenol, methyleugenol and similar phenols; amylcinnamaldehyde, anisaldehyde, n-butyraldehyde, cuminaldehyde, cyclamenaldehyde, decyl aldehyde, isobutyraldehyde, hexylaldehyde, heptylaldehyde, n-nonyl aldehyde nonadienol, citral, citronellal, hydroxycitronellal, benzaldehyde, methylnonyl acetaldehyde, cinnamaldehyde, dodecanol, hexylcinnamaldehyde, undecanal, heliotropin, vanillin, ethylvanillin and similar aldehydes, methyl amyl ketone, methyl β-naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amylbutyrolactone, diphenyl oxide, methylphenyl glycidate, nonylacetone, coumarin, cineol, ethylmethylphenyl glycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate, methyl heptinecarboxylate, methyl octinecarboxylate, isoamyl caprylate, methyl laurate, ethyl myristate, methyl myristate, ethyl benzoate, benzyl benzoate, methylcarbinylphenyl acetate, isobutylphenyl acetate, methyl cinnamate, styracin, methyl salicylate, ethyl anisate, methyl anthranilate, ethyl pyruvate, ethylbutyl butyrate, benzyl propionate, butyl acetate, butyl butyrate, p-tert-butyl cyclohexyl acetate, cedryl acetate, citronellyl acetate, citronellyl formate, p-cresyl acetate, ethyl butyrate, ethyl caproate, ethyl cinnamate, ethyl phenyl acetate, ethylene brassylate, geranyl acetate, geranyl formate, isoamyl salicylate, isoamyl valerate, isobornyl acetate, linalyl acetate, methyl anthranilate, methyl dihydrojasmonate, nonyl acetate, β-phenylethyl acetate, trichloromethylene-phenylcarbinyl acetate, terpinyl acetate, vetiveryl acetate and similar esters. These fragrances can be used individually, or at least two of them may be used in admixture with one another. Besides the fragrance, the formulation according to the invention may, if appropriate, additionally contain the additives conventionally employed in the perfume industry, such as patchouli oil or similar volatilization inhibitors, such as eugenol, or similar viscosity regulators.

The products according to the invention may also comprise deodorants such as, for example, lauryl methacrylate, geranyl crotonate, acetophenone myristate, p-methylacetophenone benzaldehyde, benzyl acetate, benzyl propionate, amylcinnamaldehyde, anisaldehyde, diphenyl oxide, methyl benzoate, ethyl benzoate, methyl phenyl acetate, ethyl phenyl acetate, neolin, saffrol and the like.

The granules according to the invention may have a certain residual moisture. In this context, it is preferred that the residual moisture of the granules is adjusted such that the starch will not swell upon storage of the granules. Moreover, it is preferred to adjust the residual moisture of the granules such that the resulting granules according to the invention are storage-stable to microbial attack, i.e. that the granules will not turn mouldy.

Preferably, these properties are obtained in the granules according to the invention without the use of preservatives, but it should be mentioned expressly that the use of a preservative in the granules according to the invention is also embraced by the present invention.

Accordingly, it is preferred that the residual moisture of the granules according to the invention is less than 25%, preferably less than 20%, especially preferably less than 14%. In this context, the storage stability of the granules, in particular at a residual moisture of less than 14%, is achieved without using preservatives in the granules according to the invention.

The granules according to the invention are essentially such that the active substances and additives are as homogeneously distributed as possible in the granules and, in contrast to untreated pulverulent mixtures, are not significantly separated into the components when the granules are transported, stored and applied.

The granules according to the invention have bulk densities of generally 50 to 1000 $g/dm^3$, preferably 90 to 800 $g/dm^3$, especially preferably 400 to 700 $g/dm^3$.

The present invention furthermore relates to a process for the preparation of granules which comprises at least one agrochemical active substance and hydrolysed starch and which is to a very high degree free from dust and separation phenomena. The process according to the invention is characterized in that the granules are prepared by means of hydrothermic-mechanical processes (for example expanding, extruding, flocculating), with or without a final structure-imparting step.

In an especially preferred embodiment of the present invention, the temperature in these processes is from 90 to 130° C.

Here, it is preferred that the granules are only briefly exposed to this temperature. For the purposes of the present invention, the term "briefly" is understood as meaning a period of a maximum of one minute, or less.

The hydrothermic-mechanical processes can be carried out in any suitable device known per se to the skilled worker. For example, these processes can be carried out in a screw extruder or in an expander. Here, the components of the granules are first mixed with one another. This granule premix is then subjected to the hydrothermic-mechanical processes.

When carrying out the process according to the invention in a screw extruder, the granule premix is, in this process, after the addition of water and/or steam, if appropriate in an upstream conditioning device, subjected to such intensive pressure, shear and thermal stress in the screw extruder that the starch of the cereal is hydrolysed and gelatinised, and that a structure is imparted to the granules. A subsequent drying and cooling process determines the residual moisture and curing of the granules.

In a further embodiment of the present invention, the hydrothermic-mechanical processes of the process according to the invention are carried out in an expander. The procedure in the preparation of the granules according to the invention can preferably proceed as follows:

First, a premix of the agrochemical active substance and a suitable required amount of a starchy substance is prepared in a mixer. This premix may, if appropriate, be mixed with further adjuvants which have been mentioned in the description of the granules according to the invention. In a conditioning device, this mixture is then treated with saturated steam and/or water and then conveyed to the hydrothermic-mechanical processes in an expander.

In a further embodiment of the process according to the invention, the hydrothermic-mechanical processes are carried out without the agrochemical active substance(s) and additives, or only with proportions of these substances, i.e. only the matrix-forming constituents of the formula of the granules according to the invention are subjected to the hydrothermic-mechanical processes. In this embodiment of the process according to the invention, the agrochemical active substance(s) and additives are sprayed at ambient pressure in liquid form, or applied in vacuo, to the granules prepared by means of the hydrothermic-mechanical processes. This procedure is always preferred when the agrochemical active substance(s) and/or the additives are not to be exposed to the hydrothermic-mechanical stress.

Independently of whether the granules according to the invention are prepared with a screw extruder or with an expander, flash evaporation takes place as the product leaves these apparatuses.

Finally, the resulting granules, which have been subjected to flash evaporation, can be comminuted, either after drying and/or cooling processes or else directly.

For example, the granules thus obtained can be comminuted in one or more steps.

Thus, it is possible in one embodiment of the process according to the invention first to carry out a precomminution of the granules obtained. This precomminution, which is effected in a primary crusher, can be effected for example with cooling, i.e. at reduced temperatures.

After the precomminution, or directly after obtaining the granules from the hydrothermic-mechanical processes with or without drying and/or cooling processes, the granule size may also be adjusted by means of a mill, in particular a cylinder mill or a sieve, for example a strainer.

In a further embodiment of the process according to the invention, it is provided to return the undersize and/or oversize particles.

The granules obtainable by this process are preferably the granules described in greater detail at the outset.

The present invention furthermore relates to granules which are obtainable by a process as described above.

The present invention furthermore relates to the use of the granules according to the invention as plant protection product, in particular for the foliar penetration and for the formulation of baits.

In this context, the granules according to the invention are preferably applied when there is still residual moisture on the leaf surfaces. For example, the granules according to the invention can be applied when the individual plants are still covered in dew. When the granules according to the invention make contact with the leaf, they essentially adhere to the leaf surface, which is provided with moisture. While the granules according to the invention adhere to the leaf, the penetrant may, for example, first make the foliar cuticle permeable to the active substance so that the active substance can penetrate into the leaf. In this context, the residence time of the granules on the leaf must be sufficiently long in order to ensure complete release of the active substance from the granules into the plant.

Preferably, the granules according to the invention are designed such that the granules dissolve after a certain period of time and no longer leave any residue on the leaves.

In order for the granules according to the invention to meet this requirement, they must not be unduly heavy and unduly large in order to adhere to the leaves. On the other hand, the granules according to the invention are preferably dust-free for handling reasons, to avoid a separation of the mixture and spreading, and for consumer acceptance reasons.

The granules can be applied by means of applicators conventionally employed for distributing granules on the soil, since the granules according to the invention are free-flowing bulk goods.

It is furthermore preferred for the agrochemical active substance in the granules to be distributed homogeneously so that a reliable activity is also possible in the case of low active substance concentration, and therefore low quantities of active substance.

The present invention is illustrated in greater detail with the aid of the examples which follow which, however, do not represent any limitation of the present invention.

EXAMPLE

The following granules are prepared with the following formulas (all information in % by weight) by means of an expander, but each of these formulas is prepared at two different expander operating conditions. The active substance is fenoxaprop-P-ethyl, and the penetrant used is Genapol® X 60.

| Constituent | No. 1 | No. 2 | No. 3 | No. 4 | No. 5 |
|---|---|---|---|---|---|
| Fenoxaprop-P-ethyl | 0.06% | 0.06% | 0.06% | 0.06% | 0.06% |
| Genapol ® X060 | 0.30% | 0.30% | 0.30% | 0.30% | 0.30% |
| Methylcellulose | 0.00% | 1.00% | 5.00% | 0.00% | 0.00% |
| Corn starch | 0.00% | 0.00% | 0.00% | 10.00% | 15.00% |
| Fine wheat flour | 99.64% | 98.64% | 94.64% | 89.64% | 84.64% |
| Total | 100% | 100% | 100% | 100% | 100% |
| Temperature at the expander head (approx.)/° C. | 110 | 110 | 110 | 110 | 110 |

| Constituent | No. 6 | No. 7 | No. 8 | No. 9 | No. 10 |
|---|---|---|---|---|---|
| Fenoxaprop-P-ethyl | 0.06% | 0.06% | 0.06% | 0.06% | 0.06% |
| Genapol ® X060 | 0.30% | 0.30% | 0.30% | 0.30% | 0.30% |
| Methylcellulose | 0.00% | 1.00% | 5.00% | 0.00% | 0.00% |
| Corn starch | 0.00% | 0.00% | 0.00% | 10.00% | 15.00% |
| Fine wheat flour | 99.64% | 98.64% | 94.64% | 89.64% | 84.64% |
| Total | 100% | 100% | 100% | 100% | 100% |
| Temperature at the expander head (approx.)/° C. | 130 | 130 | 130 | 130 | 130 |

First, a premix of micronized active substance, the penetrant and a certain amount of fine wheat flour is prepared in a mixer. This premix is mixed with the majority of the fine wheat flour and the residual components of the formula in the main mixer. In a conditioner, this mixture is admixed with water and/or saturated steam. This is followed by the hydrothermic-mechanical treatment in an expander. In a preliminary crusher, a structure is imparted to the expandate and the expandate is cooled. The granule size is adjusted by means of a cylinder mill and screening.

The biological activity of the granules against the relevant weed crabgrass is at least 72 to 95%.

The invention claimed is:

1. Granules comprising at least one agrochemical active substance and a hydrolysed starch that forms a matrix in the granules for the agrochemical active substance,
   wherein the starch is obtained from comminuted cereal and the starch content is 94.64% to 99.64% by weight,
   wherein the comminuted cereal together with the at least one agrochemical active substance are subjected to a hydrothermic-mechanical process to produce the granules, and
   wherein the granules structure in terms of mass comprises at least one of the following conditions:
   (a) $x_{10} \geqq 100$ μm
   (b) $x_{90} \leqq 5$ mm.

2. Granules according to claim 1, wherein the granules have a granule density of not more than 1.5 kg/dm$^3$.

3. Granules according to claim 1, wherein the granules have an active substance concentration no less than 0.001% by weight, where the active substance concentration can be formed by one active substance or by a mixture of several active substances.

4. Granules according to claim 1, wherein the granules have a bulk density of from 50 to 1000 g/dm$^3$.

5. Granules according to claim 1, wherein the granules further comprise at least one of constituent, filler, extender, glidant, colorant, fragrance, release agent and/or preservative.

6. A plant protection product for foliar penetration and/or for the formulation of baits comprising granules according to claim 1.

7. Granules according to claim 1, wherein the granule structure in terms of mass comprises at least one of the following conditions:
   (a) $x_{10} \geqq 400$ μm
   (b) $x_{90} \leqq 1.2$ mm.

8. Granules according to claim 1, wherein the granule structure in terms of mass comprises at least one of the following conditions:
   (a) $x_{10} \geqq 200$ μm
   (b) $x_{90} \leqq 2$ mm.

9. Granules according to claim 1, wherein the granules have a granule density of not more than 1.0 kg/dm$^3$.

10. Granules according to claim 1, wherein the granules have a bulk density of from 400-700 g/dm$^3$.

11. Granules according to claim 1, wherein a residual moisture of the granules is less than 25%.

12. A method for plant protection by applying granules according to claim 1 to a leaf surface of a plant, wherein the granules adhere to the leaf surface and release the active substance to the plant.

13. A process for the preparation of granules comprising at least one agrochemical active substance and hydrolysed starch wherein the starch content is 94.64% to 99.64% by weight, said process comprising conducting a hydrothermic-mechanical process with or without a final structure-imparting step,
   wherein the granules structure in terms of mass comprises at least one of the following conditions:
   (a) $x_{10} \geqq 100$ μgm
   (b) $x_{90} \leqq 5$ mm.

14. Granules obtainable by a process according to claim 13.

15. A process of claim 13, wherein said final structure imparting step is conducted.

16. A process according to claim 13, wherein a temperature in the process is from 90 to 130° C.

17. A bait comprising granules comprising at least one agrochemical active substance and a hydrolysed starch that forms a matrix in the granules for the agrochemical active substance,
   wherein the starch is obtained from comminuted cereal and the starch content is 94.64% to 99.64% by weight,
   wherein the comminuted cereal together with the at least one agrochemical active substance are subjected to a hydrothermic-mechanical process to produce the granules, and
   wherein the granules structure in terms of mass comprises at least one of the following conditions:
   (a) $x_{10} \geqq 100$ μm
   (b) $x_{90} \geqq 5$ mm.

18. Granules according to claim 17, wherein the granules have an:
   a. active substance concentration no less than 0.05% by weight
   b. active substance concentration no more than 7% by weight,
   where the active substance concentration can be formed by one active substance or by a mixture of several active substances.

19. Granules comprising at least one agrochemical active substance and a hydrolysed starch that forms a matrix in the granules for the agrochemical active substance,
   wherein the starch is obtained from comminuted cereal and the starch content is 90% to 99.64% by weight,
   wherein the comminuted cereal together with the at least one agrochemical active substance are subjected to a hydrothermic-mechanical process to produce the granules, and
   wherein the granules structure in terms of mass comprises at least one of the following conditions:
   (a) $x_{10} \geqq 100$ μm
   (b) $x_{90} \geqq 5$ mm.

* * * * *